United States Patent
Françon et al.

(10) Patent No.: US 6,982,088 B2
(45) Date of Patent: Jan. 3, 2006

(54) VACCINE COMPOSITION AND STABILIZATION METHOD USING HIGH MOLECULAR WEIGHT PVP

(75) Inventors: Alain Françon, Bessenay (FR); Catherine Noël, Ecully (FR)

(73) Assignee: Aventis Pasteur, S.A., Lyon Cedex (FR)

( * ) Notice: Subject to any disclaimer, the term of this patent is extended or adjusted under 35 U.S.C. 154(b) by 96 days.

(21) Appl. No.: 10/381,948

(22) PCT Filed: Oct. 8, 2001

(86) PCT No.: PCT/FR01/03097

§ 371 (c)(1),
(2), (4) Date: Mar. 31, 2003

(87) PCT Pub. No.: WO02/28362

PCT Pub. Date: Apr. 11, 2002

(65) Prior Publication Data

US 2003/0190331 A1    Oct. 9, 2003

(30) Foreign Application Priority Data

Oct. 6, 2000  (FR) .................................. 00/12805

(51) Int. Cl.
*A61K 39/12*    (2006.01)
(52) U.S. Cl. .............. 424/204.1; 424/184.1; 424/216.1; 424/278.1
(58) Field of Classification Search ............ 424/184.1, 424/204.1, 216.1, 278.1
See application file for complete search history.

(56) References Cited

U.S. PATENT DOCUMENTS

| 3,915,794 A | | 10/1975 | Zygraich et al. |
| 3,919,411 A | | 11/1975 | Glass et al. |
| 5,695,770 A | * | 12/1997 | Raychaudhuri et al. .. 424/278.1 |
| 5,792,643 A | * | 8/1998 | Herrmann et al. ....... 435/235.1 |
| 6,379,677 B1 | * | 4/2002 | Klesius et al. ........... 424/244.1 |

FOREIGN PATENT DOCUMENTS

| EP | 0273512 A | 7/1988 |
| WO | 94 15636 | 7/1994 |

OTHER PUBLICATIONS

The Merck Index: an Encyclopedia of Chemical and Drugs, Ninth edition, Windholz Ed., published by Merck & Co. Inc, Rahway, NJ, 1976, p. 7483.*
The Merck Index: an Encyclopedia of Chemical and Drugs, Ninth edition, Windholz Ed., published by Merck & Co. Inc, Rahway, NJ, 1976, p. 996.*

* cited by examiner

*Primary Examiner*—Jeffrey Stucker
(74) *Attorney, Agent, or Firm*—McDonnell Boehnen Hulbert & Berghoff LLP.

(57) ABSTRACT

The invention concerns the stabilization of a vaccine composition maintained in liquid state by the use of high molecular weight polyvinylpyrrolidone, hence eliminating the use of albumen. The invention is of particular interest for vaccine compositions comprising attenuated live viruses such as oral vaccine against poliomyelitis.

16 Claims, No Drawings

VACCINE COMPOSITION AND STABILIZATION METHOD USING HIGH MOLECULAR WEIGHT PVP

This application is a National Stage of International Application No. PCT/FR01/03097 filed Oct. 8, 2001.

The present invention relates to the field of vaccines. More particularly, the invention relates to the stabilizing of liquid vaccines.

One of the major problems in the field of vaccines is their stability, that is to say the preservation of their efficacy over time. One of the solutions proposed for solving the problem of stability is freeze-drying. This solution, which is satisfactory from a technical point of view, nevertheless has disadvantages: on the one hand, it represents, for the industrialist, an additional step, which increases the cost and the duration of manufacture, and, on the other hand, it involves, for the user, an operation prior to the administration of the product: the operation of taking up the freeze-dried product.

Another solution proposed in the prior art for preserving the efficacy of vaccines over time is to use stabilizing formulations which generally comprise albumin. However, the risks of contamination presented by the use of albumin of human or animal origin, as well as the very high costs linked to the use of recombinant albumin, have led to the search for substitutes for albumin for stabilizing liquid vaccines.

The replacement of albumin has already been sought for other pharmaceutical applications. Thus, U.S. Pat. No. 3,915,794 proposes replacing animal proteins such as albumin or casein with low-molecular-weight polyvinylpyrrolidone (PVP) during the phase for extracting the viruses from cells as well as during the freeze-drying stage which takes place subsequently. However, a product capable of replacing albumin in some of its functions is not always effective for other applications and cannot therefore be considered as a universal substitute for albumin.

Tests for stabilizing liquid vaccines over time have thus been carried out with low-molecular-weight PVP which is described in the abovementioned U.S. patent; however, these tests have not led to satisfactory results.

A need therefore exists to find formulations free of albumin and capable of stabilizing liquid vaccine compositions, in particular compositions comprising viruses, and in particular attenuated live viruses.

To achieve this aim, the invention proposes a method for stabilizing a vaccine composition in the liquid state according to which high-molecular-weight polyvinylpyrrolidone is added to the vaccine composition.

The subject of the invention is also a liquid vaccine composition which is stable over time, characterized in that it comprises at least one viral antigen, and at least high-molecular-weight polyvinyl-pyrrolidone.

According to a particular characteristic of the invention, the molecular weight of the PVP is greater than or equal to 100 000 daltons.

According to another characteristic of the invention, the PVP is used at a concentration of at least 0.1% by weight, and preferably of less than or equal to 5%.

According to another characteristic of the invention, the vaccine composition comprises attenuated live viruses. It may be in particular a vaccine composition against poliomyelitis, intended for oral administration.

According to another characteristic of the invention, the vaccine composition comprises, in addition, salts or sugars as well as at least one surfactant. Under these conditions, the stability results obtained are particularly satisfactory.

Other characteristics of the invention will emerge during the detailed description which follows.

The vaccine compositions, whose stability over time has to be provided for, are vaccine compositions comprising at least one antigen consisting of a virus. The stability of such compositions is assessed, according to criteria defined by the various regulatory authorities, by the preservation, over time, of the infectious titre of the vaccine composition, which means that the viruses used as antigens should preserve their capacity to infect cells.

Among the vaccine compositions which can be used according to the method of the invention, there may be mentioned the vaccines comprising attenuated live viruses and, in particular, vaccines against poliomyelitis. This may include monovalent vaccine compositions, that is to say intended for protecting against a single disease (although they may comprise several types of the same valency, as is the case with poliomyelitis and Dengue for example) or multivalent compositions, that is to say vaccines intended for protecting against several diseases, at least one of the valencies consisting of an attenuated live virus as described above.

The method according to the invention has shown its full value in stabilizing the oral vaccine against poliomyelitis, which is an attenuated live virus vaccine comprising 3 types of poliomyelitis virus.

According to the invention, the vaccine composition is stabilized by means of an addition of high-molecular-weight polyvinylpyrrolidone (or PVP), in particular PVP360 whose MW is 360 000 daltons. Indeed, against all expectations, while the low-molecular-weight PVP described in the prior art as stabilizing factor during the phase for extracting the viruses as well as during the freeze-drying phase and the phase for storing the freeze-dried product did not make it possible to satisfactorily stabilize a vaccine composition in the liquid state, it was found that the high-molecular-weight PVP made it possible to very advantageously replace the albumin normally used in the stabilizing formulations for liquid vaccine compositions. The good quality of the results obtained is all the more surprising since it is in contradiction with the teaching of U.S. Pat. No. 3,915,794, according to which PVP K90 which has an MW of 360 000 is not satisfactory for stabilizing a viral suspension.

PVP is a synthetic chemical product; its origin is not critical with regard to the present invention, provided that it is of a pharmaceutically acceptable quality. Thus, the PVP360 provided by SIGMA is perfectly suitable for use according to the present invention.

The concentration of PVP is at least equal to 0.1% by weight/volume. So as to have no problem linked to the viscosity of the medium, it is however desirable not to exceed a concentration of 5%. Good results were obtained with a concentration of 1%.

Advantageously, the vaccine composition according to the invention also comprises a certain quantity of surfactant, such as polyethylene glycol (or PEG). It is also possible to use Tween™ 80 or Polysorbate 80. The quantity of surfactant used is preferably a quantity of less than 0.007% by weight/volume. A quantity of Tween™ 80 of 0.004% gave particularly good results.

According to one characteristic of the invention, the vaccine composition comprises, in addition, salts such as magnesium chloride $MgCl_2$, in a substantially molar concentration; the vaccine composition may also comprise sugars such as glucose and sucrose whose concentrations may vary from about 20% to about 40%; however, the presence of these sugars is not critical for the stabilizing effect.

The vaccine composition may also comprise any other component usually used in vaccines, such as preservatives and/or adjuvants. It may in particular comprise buffer substances such as the Hepes buffer in a concentration equal to about 20 mM.

The examples which follow illustrate particular embodiments of the present invention.

EXAMPLE 1

Viral suspensions of 3 different types of poliomyelitis are produced in the following manner: A biogenerator containing Vero cells at the 142nd passage, in Parker 199 medium, is inoculated with one of the types of polio virus. The viral culture is carried out at a temperature of about 34° C. After a period not exceeding 96 hours, the cell lysis being complete, the viral harvest is performed by recovering the supernatant. The harvest is filtered on membrane having a cut-off at 100 000, and then purified by passage on a DEAE Spherodex column equilibrated beforehand to pH 7 in 40 mM phosphate buffer. Under these conditions, the impurities are retained by the column while the viruses pass through it freely.

The viral suspension which has passed through the column is then filtered on membrane having a cut-off at 10 000, and then subjected to zonal ultracentrifugation on sucrose gradient; the fraction of interest is that present at 45–55% sucrose.

A monovalent suspension of a given type (I, II or III) of polio virus is thus obtained.

EXAMPLE 2

Vaccine compositions are prepared from the monovalent compositions prepared in Example 1, by mixing:

type I viral suspension, type II viral suspension, type III viral suspension, in quantities which make it possible to obtain, in a volume of 100 ml, a titre, for each of the strains, of 6.3 log 10CCID50/dose, to which one of the following mixtures is added so as to obtain compositions whose stability it is desired to test:

- 1% albumin, 1 M $MgCl_2$, 20 mM Hepes buffer, 0.002% Tween™ 80,
- PVP360, 1 M $MgCl_2$, 20 mM Hepes buffer,
- PVP360 at various concentrations, 1 M $MgCl_2$, 20 mM Hepes buffer, and Tween™ 80 at various concentrations,
- PVP360 at various concentrations, 20 mM Hepes buffer, 0.002% Tween™ 80 and sugars (glucose and sucrose) at various concentrations,
- PVP10 at various concentrations, 1 M $MgCl_2$, 20 mM Hepes buffer, and 0.002% Tween™ 80, or
- PVP40 at various concentrations, 1 M $MgCl_2$, 20 mM Hepes buffer, and 0.002% Tween™ 80.

Various compositions are kept for 5 days at 37° C., i.e. under conditions which are accelerated ageing conditions which make it possible to evaluate the stability of the compositions obtained.

EXAMPLE 3

The stability of the viral compositions prepared is evaluated by assessing the reduction in the infectious titre over time. The determination of the infectious titre is carried out by the CCID50 technique which is carried out in the following manner:

The titration is carried out in 96-well microplates. The samples are diluted −1 to −6 or −7 (as log 10) in MEM medium 1×C with 2% (volume/volume) of foetal calf serum containing no antibodies against polio, 4% (volume/volume) of 5.6% sodium bicarbonate (volume/volume) without phenol red and 0.2% of a solution of penicillin-didromycin antibiotic 400×C (volume/volume). For each dilution, 50 μl are distributed in 4 rows of 10 wells:

- in the 1st row, 50 μl of dilution medium are added (overall titre)
- in the 2nd row, 50 μl of anti-polio type 2 antiserum plus anti-polio type 3 antiserum diluted in MEM medium are added so as to neutralize the type 2 and 3 polio viruses contained in the vaccine composition (titration of type I),
- in the 3rd row, 50 μl of anti-polio type 1 antiserum plus anti-polio type 3 antiserum diluted in MEM medium are added so as to neutralize the polio type 1 and 3 viruses contained in the vaccine composition (titration of type II),
- in the 4th row, 50 μl of anti-polio type 1 antiserum plus anti-polio type 2 antiserum diluted in MEM medium are added so as to neutralize the type 1 and 2 polio viruses contained in the vaccine composition (titration of type III).

The 8 wells of the last column of each of the plates serve as control cells: 100 μl of MEM medium are added thereto per well.

The plates are covered with a cover; they are shaken sideways and the medium is left in contact for 1 hour at 37° C.

After this contact time, 100 μl of HepII cell suspension are added to each well at 50 000 cells/ml. The plates are placed for 9 days in an incubator at 36° C.

To prepare the cell suspension, the procedure should be carried out in the following manner: [dissociate] the cells by the action of trypsin, enumerate and dilute the cell suspension so as to obtain a concentration of 50 000 cells/ml.

The pathogenic effects are read in each of the wells after having checked the integrity of the control cells.

Calculation of the titre is carried out using a linear regression on the various dilutions after converting the data to the arc sine of the root of the proportions of positive wells.

The assays are carried out, for each of the viral compositions prepared, at T0 and after 5 days at 37° C.

The results obtained, expressed as the difference between the titre at T0 and the titre after accelerated ageing for 5 days at 37° C., are summarized in the table below; they are considered to be satisfactory when they are substantially equivalent to or less than those obtained with a vaccine composition of the prior art, i.e. stabilized with 1% albumin.

| | Type 1 | Type 2 | Type 3 | Global |
|---|---|---|---|---|
| Albumin 1% + $MgCl_2$ + Hepes + Tween 0.002% | 0.82 | 0.67 | 0.67 | 0.67 |
| PVP360 1% + $MgCl_2$ + Hepes | 0.06 | 0.22 | 0.07 | 0.17 |
| PVP360 1% + $MgCl_2$ + Hepes + Tween 0.002% | 0.85 | 0.75 | 0.85 | 0.85 |
| PVP360 2% + $MgCl_2$ + Hepes + Tween 0.002% | 1.00 | 0.85 | 0.60 | 0.75 |
| PVP360 5% + $MgCl_2$ + Hepes + Tween 0.002% | 1.13 | 0.67 | 1.22 | 1.43 |
| PVP360 10% + $MgCl_2$ + Hepes + Tween 0.002% | 1.80 | 1.50 | 1.65 | 1.65 |
| PVP360 0.1% + $MgCl_2$ + Hepes + Tween 0.004% | 1.20 | 1.45 | 0.90 | 1.20 |
| PVP360 0.5% + $MgCl_2$ + Hepes + Tween 0.004% | 0.60 | 0.70 | 0.55 | 0.75 |
| PVP360 1% + $MgCl_2$ + Hepes + Tween 0.004% | 0.72 | 0.59 | 0.87 | 0.68 |
| PVP360 1.5% + $MgCl_2$ + Hepes + Tween 0.004% | 0.90 | 0.55 | 0.85 | 0.85 |
| PVP360 2.5% + $MgCl_2$ + Hepes + Tween 0.004% | 0.82 | 1.05 | 0.95 | 0.53 |
| PVP360 4.9% + $MgCl_2$ + Hepes + Tween 0.004% | 1.00 | 0.85 | 1.25 | 0.75 |
| PVP360 1% + $MgCl_2$ + Hepes + Tween 0.006% | 0.85 | 0.55 | 0.85 | 0.65 |
| PVP360 2% + $MgCl_2$ + Hepes + Tween 0.006% | 0.50 | 0.70 | 1.00 | 0.45 |
| PVP360 1.3% + $MgCl_2$ + Hepes + Tween 0.007% | 0.85 | 0.80 | 1.00 | 0.80 |
| PVP360 3.7% + $MgCl_2$ + Hepes + Tween 0.007% | 1.05 | 0.70 | 1.25 | 0.80 |
| PVP360 2.5% + Hepes + Tween 0.002% + glucose 20% + sucrose 40% | 1.45 | 1.20 | 0.95 | 1.20 |
| PVP360 1.25% + Hepes + Tween 0.002% + glucose 30% + sucrose 40% | 1.35 | 1.10 | 0.80 | 1.05 |
| PVP360 1.25% + Hepes + Tween 0.002% + glucose 20% + sucrose 28% | 1.00 | 0.85 | 0.40 | 0.95 |
| PVP10 5% + $MgCl_2$ + Hepes + Tween 0.002% | 2.15 | 2.10 | 2.00 | 2.30 |
| PVP10 10% + $MgCl_2$ + Hepes + Tween 0.002% | 2.10 | 2.45 | 2.10 | 2.15 |
| PVP10 30% + $MgCl_2$ + Hepes + Tween 0.002% | 2.65 | 2.85 | 2.55 | 3.10 |
| PVP40 5% + $MgCl_2$ + Hepes + Tween 0.002% | Titre less than 3.50 after accelerated ageing | | | 3.55 |
| PVP40 10% + $MgCl_2$ + Hepes + Tween 0.002% | Titre less than 3.50 after accelerated ageing test | | | |
| PVP40 30% + $MgCl_2$ + Hepes + Tween 0.002% | | | | |

What is claimed is:

1. A method for stabilizing over time a vaccine composition in the liquid state, the method comprising combining the vaccine composition with high-molecular-weight polyvinylpyrrolidone having a molecular weight greater than or equal to 100,000.

2. The method according to claim 1, wherein the concentration of polyvinylpyrrolidone is at least 0.1%.

3. The method according to claim 1, wherein the concentration of polyvinylpyrrolidone is less than or equal to 5%.

4. The method according to claim 1, further comprising adding to the vaccine composition magnesium chloride in a substantially molar concentration.

5. The method according to claim 1, further comprising adding to the vaccine composition at least one surfactant at a concentration of less than or equal to 0.007%.

6. The method according to claim 5, wherein the surfactant is Polysorbate 80 in a concentration equal to 0.004%.

7. The method according to claim 1, wherein the vaccine composition comprises at least one antigen consisting of an attenuated live virus.

8. The method according to claim 7, wherein the vaccine composition comprises the 3 serotypes of the poliomyelitis virus.

9. A liquid vaccine composition which is stable over time comprising at least one viral antigen and at least high-molecular-weight polyvinylpyrrolidone having a molecular weight of greater than or equal to 100,000.

10. The composition according to claim 9, wherein the concentration of polyvinylpyrrolidone is at least 0.1%.

11. The composition according to claim 9, wherein the concentration of polyvinylpyrrolidone is less than or equal to 5%.

12. The composition according to claim 9, further comprising magnesium chloride in a substantially molar concentration.

13. The composition according to claim 9, further comprising at least one surfactant at a concentration of less than or equal to 0.007%.

14. The composition according to claim 13, wherein the surfactant is Polysorbate 80 in a concentration equal to 0.004%.

15. The composition according to claim 9, wherein the viral antigen is an attenuated live virus.

16. The composition according to claim 15, wherein the vaccine composition comprises the 3 serotypes of the poliomyelitis virus.

* * * * *